United States Patent
Sanders

(10) Patent No.: US 10,195,180 B2
(45) Date of Patent: Feb. 5, 2019

(54) METHODS AND COMPOSITIONS FOR TREATING FOOT OR HAND PAIN

(71) Applicant: Jennifer L. Sanders, San Francisco, CA (US)

(72) Inventor: Jennifer L. Sanders, San Francisco, CA (US)

( * ) Notice: Subject to any disclaimer, the term of this patent is extended or adjusted under 35 U.S.C. 154(b) by 0 days.

(21) Appl. No.: 14/231,096

(22) Filed: Mar. 31, 2014

(65) Prior Publication Data

US 2014/0213625 A1 Jul. 31, 2014

Related U.S. Application Data

(63) Continuation of application No. PCT/US2012/058907, filed on Oct. 5, 2012.

(60) Provisional application No. 61/543,445, filed on Oct. 5, 2011.

(51) Int. Cl.
| | |
|---|---|
| A61K 9/00 | (2006.01) |
| A61K 31/135 | (2006.01) |
| A61K 31/195 | (2006.01) |
| A61K 31/197 | (2006.01) |
| A61K 31/4174 | (2006.01) |

(52) U.S. Cl.
CPC ........ *A61K 31/4174* (2013.01); *A61K 9/0014* (2013.01); *A61K 31/135* (2013.01); *A61K 31/195* (2013.01); *A61K 31/197* (2013.01)

(58) Field of Classification Search
CPC .. A61K 31/135; A61K 31/195; A61K 31/197; A61K 31/4174; A61K 9/0014
See application file for complete search history.

(56) References Cited

U.S. PATENT DOCUMENTS

| | | | |
|---|---|---|---|
| 3,670,087 A | 6/1972 | Lorenzetti | |
| 6,103,771 A | 8/2000 | Galer et al. | |
| 6,979,441 B2 | 12/2005 | Crandall | |
| 7,074,198 B2 | 7/2006 | Krullaards | |
| 7,666,914 B2* | 2/2010 | Richlin | A61K 9/0014 424/428 |
| 7,812,049 B2 | 10/2010 | Shanler et al. | |
| 7,838,563 B2 | 11/2010 | DeJovin et al. | |
| 7,973,068 B2 | 7/2011 | Demopulos et al. | |
| 8,114,898 B2 | 2/2012 | Shanler et al. | |
| 8,304,402 B2 | 11/2012 | Binder | |
| 8,420,688 B2 | 4/2013 | Shanler et al. | |
| 8,426,410 B2 | 4/2013 | DeJovin et al. | |
| 8,617,583 B2 | 12/2013 | King | |
| 8,685,439 B2 | 4/2014 | Chapin et al. | |
| 8,883,838 B2 | 11/2014 | Shanler et al. | |
| 8,956,641 B2 | 2/2015 | Zanella et al. | |
| 2002/0044966 A1 | 4/2002 | Bartholomaeus et al. | |
| 2003/0082214 A1* | 5/2003 | Williams | A61K 9/0014 424/400 |
| 2003/0096807 A1 | 5/2003 | Demopulos et al. | |
| 2003/0149379 A1 | 8/2003 | Krullaards | |
| 2004/0006052 A1 | 1/2004 | Gudas et al. | |
| 2004/0147534 A1* | 7/2004 | Foote | A61K 9/0014 514/263.32 |
| 2004/0204413 A1* | 10/2004 | Faour | A61K 9/0004 514/248 |
| 2005/0168079 A1 | 7/2005 | Shanler et al. | |
| 2005/0276830 A1 | 12/2005 | DeJovin et al. | |
| 2006/0148903 A1 | 7/2006 | Burch et al. | |
| 2006/0171974 A1 | 8/2006 | DeJovin et al. | |
| 2008/0153808 A1 | 6/2008 | Gil et al. | |
| 2009/0060852 A1 | 3/2009 | DeJovin et al. | |
| 2009/0117167 A1 | 5/2009 | Burch et al. | |
| 2009/0136598 A1 | 5/2009 | Chapin et al. | |
| 2009/0202467 A1 | 8/2009 | Bock | |
| 2009/0263450 A1 | 10/2009 | Zanella et al. | |
| 2010/0029618 A1 | 2/2010 | Gil et al. | |
| 2010/0035992 A1 | 2/2010 | Bhushan et al. | |
| 2010/0130502 A1 | 5/2010 | DeJovin et al. | |
| 2010/0226972 A1* | 9/2010 | Lutz | A61K 9/0014 424/450 |
| 2011/0014259 A1 | 1/2011 | King | |
| 2012/0149748 A1* | 6/2012 | Shanler | A61K 9/0014 514/401 |

FOREIGN PATENT DOCUMENTS

| | | |
|---|---|---|
| AT | 501041 | 6/2006 |
| AT | 501041 A4 * | 6/2006 |
| WO | 02/05851 A2 | 1/2002 |
| WO | WO 2002/005851 | 1/2002 |
| WO | 2009/129432 A2 | 10/2009 |
| WO | 2009/129456 A2 | 10/2009 |
| WO | 2009/129494 A2 | 10/2009 |
| WO | WO 2009/129432 | 10/2009 |
| WO | WO 2009/129456 | 10/2009 |
| WO | WO 2009/129494 | 10/2009 |
| WO | 2010/001391 A1 | 1/2010 |
| WO | WO 2010/001391 | 1/2010 |
| WO | 2010/036937 A1 | 4/2010 |
| WO | WO 2010/036937 | 4/2010 |

OTHER PUBLICATIONS

Berge et al. "Pharmaceutical Salts," Journal of Pharmacuetical Sciences, Jan. 1977, 66 (1): pp. 2-19.*
Derwent Abstract of AT 501041 A4—Original Document Publication Date: Jun. 2006.*
Berge, S.M., et al. Pharmaceutical salts. Journ. Pharm. Sci. 66(1): 1-19 (1977).
Derwent Abstract of AT 501041—Original Publication Date Jun. 15, 2006.

* cited by examiner

Primary Examiner — Sreenivasan Padmanabhan
Assistant Examiner — Jody L Karol
(74) *Attorney, Agent, or Firm* — Young Basile Hanlon & MacFarlane, P.C.

(57) ABSTRACT

The present disclosure provides novel formulations for treating foot or hand pain by topically administering a sympathomimetic drug, particularly oxymetazoline, to the skin of the foot or hand.

14 Claims, 2 Drawing Sheets

METHODS AND COMPOSITIONS FOR TREATING FOOT OR HAND PAIN

Figure 1:
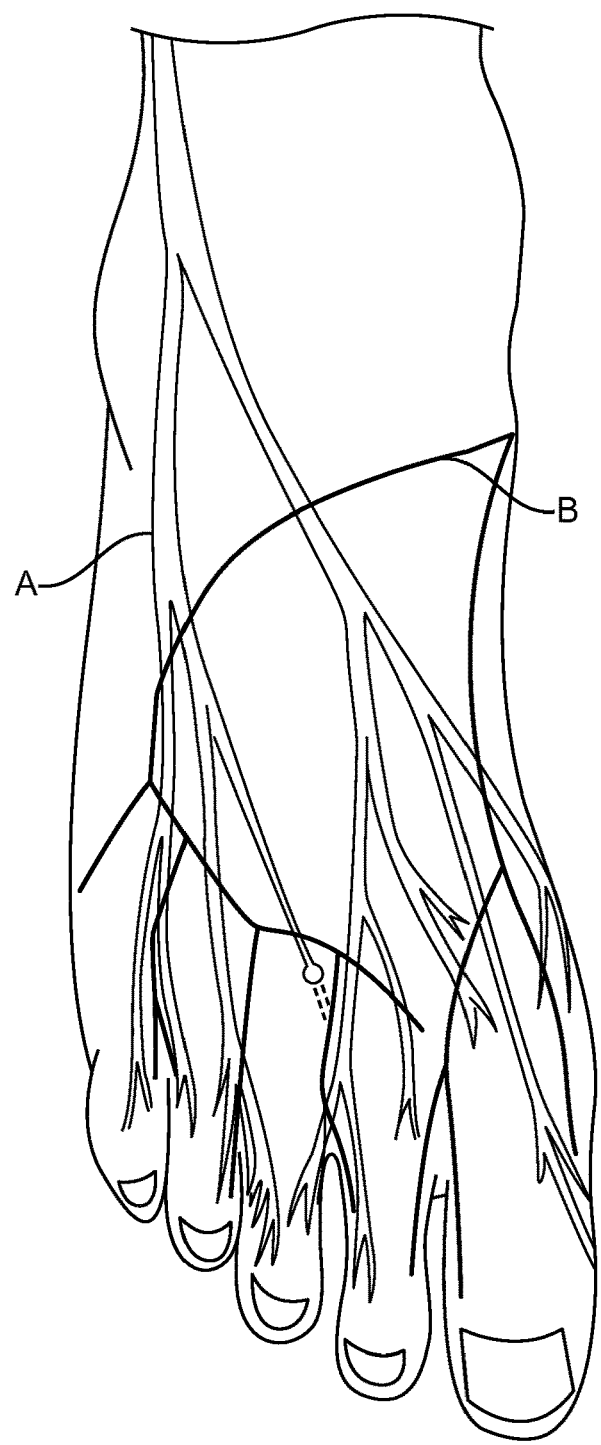

This application is a continuation of co-pending international patent application PCT/US2012/058907 (designating the United States) filed on 5 Oct. 2012, which application claims the benefit of U.S. Provisional Application No. 61/543,445, filed 5 Oct. 2011.

I. FIELD OF THE INVENTION

The present invention relates to methods and pharmaceutical compositions or formulations for treating pain associated with compression neuropathy by topical application of a sympathomimetic drug, particularly an α1 agonist, more particularly oxymetazoline.

II. BACKGROUND

Foot ailments are among the most common types of human suffering. The foot is required to support and move significant amounts of weight upon a very small surface area, which necessarily requires flexibility and adaptability. Accordingly, foot ailments may evolve into significant problems and be attendant with great pain. Among these foot ailments are interdigital neuritis and compression neuritis.

Interdigital neuritis or neuroma, more commonly known as Morton's neuroma or "foot neuroma," is a common disease entity of the foot. Neuroma pain can range from mild to severe and typically presents as numbness, burning, tingling or sharp, shooting pain in the ball of the foot or between the toes. In severe cases the pain can be debilitating to the point that a person does not want to walk or even put their foot down. Women are more likely than men to experience this condition.

Tarsal tunnel syndrome arises from the compression of the posterior tibial nerve that produces symptoms along the nerve running from the medial aspect of the ankle down to the foot. The tarsal tunnel is a narrow space at the medial aspect of the ankle. The structures contained within the tunnel are the tibialis posterior tendon, flexor digitorum longus tendon, posterior tibial artery, posterior tibial vein, posterior tibial nerve and flexor hallucis longus muscle covered by flexor retinaculum. Symptoms arise due to compression of these structures within the tarsal tunnel specifically the posterior tibial nerve. An enlarged or abnormal structure that occupies space within the tunnel can compress the nerve for example an engorged or bounding artery. Also an injury, such as an ankle sprain, may produce inflammation and swelling in or near the tunnel, resulting in compression of the nerve. Symptoms of tarsal tunnel syndrome include painful burning, tingling, or numb sensations around the ankle and toes that becomes worse after standing for long periods of time. Pain is worse with activity and is relieved by rest. There can be "electric shock sensations" radiating up into the leg and down into the arch, heel, and toes. There can be hot and cold sensations in the feet and "pins and needles"-type feeling with increased sensation on the feet. Sometimes symptoms occur suddenly, often brought on or aggravated by overuse of the foot, such as prolonged standing, walking, exercising, or beginning a new exercise program. Early treatment of tarsal tunnel syndrome is important because left untreated, the condition may progress and can result in permanent nerve damage in the nerve compression is significant over a long period of time.

Current treatment modalities for both interdigital neuritis and tarsal tunnel syndrome have high failure rates and can lead to complications. These treatments typically address the inflamed nerve without identifying the cause of the inflammation. Current treatments interdigital neuritis include changes in shoes, padding, orthoses, injections of corticosteroids, injections of denatured alcohol and when all else fails, surgical excision. For tarsal tunnel syndrome, a variety of treatment options are used, often in combination to treat tarsal tunnel syndrome. These options include: rest, ice, nonsteroidal anti-inflammatory, immobilization, physical therapy, injected corticosteroid, orthotic devices, supportive shoes and surgical decompression of the nerve. Such methods of treating interdigital neuritis and/or tarsal tunnel syndrome each have uncertain success rates, significant limitations and the potential for complications Changes in shoes: It is believed that a shoe that is too narrow in the forefoot will cause nerve irritation due to forefoot compression leading to interdigital neuritis. For this reason patients are recommended to change their shoes to a wider width to alleviate these compression forces. Unfortunately wearing wide shoes at all times is impractical for many due to their occupation and even when changes to wider shoes are made, interdigital neuritis may still persist. Furthermore, interdigital neuritis may even present in the absence of shoes entirely, becoming painful only when patients are barefoot.

Padding: Metatarsal pads are frequently applied to the shoe insole underneath the forefoot to separate the crowded metatarsals believed to be causing nerve inflammation. There is no standard thickness, size or placement of pad making reproducibility and accurate placement difficult if not impossible from shoe to shoe.

Orthoses: Orthoses are used to prevent or treat interdigital neuritis. For this purpose, orthoses providing support underneath the metatarsals are used to increase the intermetatarsal distance by reducing forefoot pronation and metatarsal hypermobility. There is no agreement whether non-custom orthoses, custom orthoses, anti-pronation or anti-supination orthoses are the most effective for patients having neuroma and orthoses cannot be worn in all styles of shoes. Similarly, orthotic devices and supportive shoes are used for tarsal tunnel syndrome, with the goal of maintaining the arch and limiting excessive motion that can cause compression of the nerves in the tarsal tunnel.

Injections: There are two types of injection for interdigital neuroma and two types of injection for tarsal tunnel syndrome. The first, for both interdigital neuritis and tarsal tunnel, is a corticosteroid injection which is designed to reduce nerve inflammation. The second injection for interdigital neuritis is a sclerosing or denatured alcohol injection to destroy the nerve at the point of inflammation. The second injection for tarsal tunnel syndrome is a local anesthetic simply to provide pain relief. Potential complications for both methods include infection and allergic reaction. In the case of corticosteroids, there is also the possibility of skin or muscle atrophy and pigment changes in the skin.

Surgery: In cases when conservative measures fail, surgical resection of the inflamed nerve is undertaken to treat interdigital neuritis. This surgery carries a risk of formation of an amputation stump following resection of the nerve. Similarly, when conservative treatment fails, surgical decompression of the tibial nerve at the tarsal tunnel is used to treat tarsal tunnel syndrome. During surgery the skin is incised and the tarsal tunnel is opened. The tibial nerve is identified and followed into the foot, where all compression points are released. In addition to the potential for infection, painful scars at the incision site also can form.

III. SUMMARY OF THE INVENTION

One aspect of the invention provides methods of treating foot or hand pain comprising topically applying to skin of a foot or hand a composition comprising a pharmaceutically effective amount of sympathomimetic drug or pharmaceutically acceptable salt thereof and a dermatologically acceptable vehicle, wherein the composition constricts blood flow in the foot or hand. In some implementations, the sympathomimetic drug is an alpha adrenergic agonist, particularly an α1 agonist, more particularly oxymetazoline. In certain implementations, the composition is topically applied to the foot or hand one or more times per day, for example, twice per day. In certain implementations, particularly for interdigital or compression neuritis, the composition is topically applied to the sole of the foot. In yet other implementations, particularly for treatment of tarsal tunnel syndrome, the composition is topically applied to the inside and/or bottom of the heel of the foot. In other implementations, the composition is topically applied to the dorsal surface of the foot. In certain implementations, the composition is topically applied to the heel of the hand, the dorsal surface of the hand, the palm of the hand and/or at the wrist.

Another aspect of the invention provides methods of treating localized hypertension in a foot or hand, said method comprising applying, to skin of a foot or hand, a composition comprising a pharmaceutically effective amount of sympathomimetic drug or pharmaceutically acceptable salt thereof and a dermatologically acceptable vehicle, wherein the composition constricts blood flow in the foot. In one implementation, the localized hypertension is caused by exercise or other repetitive compression of the foot. In some implementations, the sympathomimetic drug is an alpha adrenergic agonist, particularly an α1 agonist, more particularly oxymetazoline.

One aspect of the invention provides a pharmaceutical composition, suitable for application to the foot of a subject, comprising a pharmaceutically effective amount of sympathomimetic drug or pharmaceutically acceptable salt thereof and a dermatologically acceptable vehicle. In some implementations, the sympathomimetic drug is an alpha adrenergic agonist, particularly an α1 agonist, more particularly oxymetazoline. In certain implementations, the composition comprises 0.1% (w/w) to 5% (w/w) oxymetazoline HCl. In some implementations, the pharmaceutically effective amount of sympathomimetic drug is between 0.1% (w/w) and 5% (w/w) of the composition. In certain implementations, the composition further comprises an active agent selected from the group consisting of GABAergic agents, muscle relaxants and tricyclic antidepressants. Certain aspects of the invention provide use of the aforementioned compositions for treating foot and/or hand pain, including for treating interdigital neuritis, compression neuritis, tarsal tunnel syndrome and carpal tunnel syndrome.

Another aspect of the invention includes use of a pharmaceutically effective amount of a sympathomimetic drug, particularly an α1 agonist, for treatment of foot pain associated with interdigital or compression neuritis. In yet another aspect, the invention provides use of a sympathomimetic drug, particularly an α1 agonist, in the preparation of a medicament for treating foot pain associated with interdigital or compression neuritis.

Another aspect of the invention provides use of a pharmaceutically effective amount of oxymetazoline for treatment of tarsal tunnel syndrome. In yet another aspect, the invention provides use oxymetazoline in the preparation of a medicament for treating tarsal tunnel syndrome.

Yet another aspect of the invention provides use of a pharmaceutically effective amount of oxymetazoline for treatment of carpal tunnel syndrome. In another aspect, the invention provides use of oxymetazoline in the preparation of a medicament for treating carpal tunnel syndrome.

IV. BRIEF DESCRIPTION OF THE DRAWINGS

FIG. 1 illustrates the skeletal and vascular anatomy of the foot. A: peripheral nerves in the foot; B: arteries in the foot.

Figure 2:
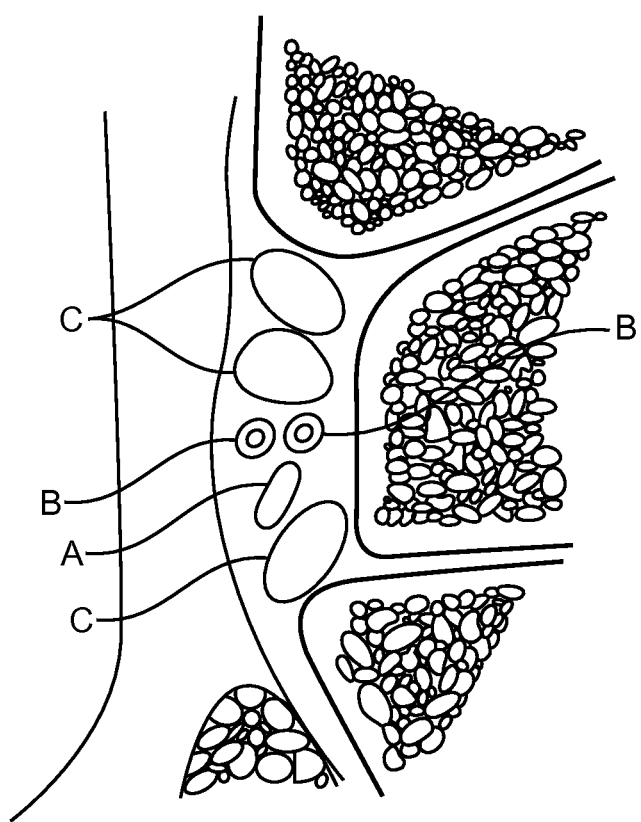

FIG. 2 illustrates the skeletal and vascular anatomy of the tarsal tunnel. A: posterior tibial nerve; B: blood vessels; C: tendons.

V. DETAILED DESCRIPTION

The present disclosure provides novel formulations for treating foot and/or hand pain by topically administering a sympathomimetic drug to the skin of the foot and/or hand.

Interdigital neuroma commonly is believed to be due to an entrapment by the metatarsal bones of a nerve that passes into the toes of the foot. The conventional hypothesis attribute this type of pain in the ball of the foot on wearing shoes that are too narrow or with very flimsy soles, or in the case of women, high heel shoes. The common hypothesis suggests that the entrapment of the nerve leads to inflammation and a thickening of the nerve. With the advent of ultrasound technology, diagnostic imaging of the neuroma has been helpful in identifying the presence, location and size of a neuroma. Utilizing ultrasound technology, the present inventor has made the unexpected observation that the neuroma often is located in close proximity to a strongly pulsing artery in the interdigital space. While not being limited to a specific theory of the invention, the present invention provides a method of relieving the symptoms of interdigital neuritis by administering a vasoconstricting sympathomimetic drug to the foot, thereby relieving any irritation to the nerve caused by the strong arterial pulse. Similarly, activities involving rapid compression or striking of the foot, such as jogging or cycling, can increase blood flow and pulsing, thereby irritating nerves in the foot.

Tarsal tunnel syndrome commonly is believed to be due to compression of the posterior tibial nerve as it passes through the tarsal tunnel. The causes of tarsal tunnel syndrome are not definitively understood. However, anything that creates pressure in the tarsal tunnel can cause pain. Such causes can include benign tumor or cysts, bone spurs, and inflammation particularly of the tendon sheath or of the surrounding are due to an ankle sprain or break. It is also believed that flat feet may increase pressure in the tarsal tunnel region leading to compression of the posterior tibial nerve. As is the case with interdigital neuritis as discuss above, the posterior tibial nerve is located in close proximity to a strongly pulsing artery in the tarsal tunnel (see FIG. 2). While not being limited to a specific theory of the invention, the present invention provides a method of relieving the symptoms of tarsal tunnel syndrome by administering a vasoconstricting sympathomimetic drug to the heel of the foot, thereby relieving any irritation to the nerve caused by the strong arterial pulse.

The invention provides a pharmaceutical composition comprising a sympathomimetic drug or a salt thereof for topical application to a foot or hand. Sympathomimetic drugs are those whose effects mimic the effects seen with activation of the sympathetic nervous system. The sympathetic nervous system liberates norepinephrine and epinephrine. Norepinephrine and epinephrine bind to two general classes of receptors, the α- and β-adrenergic receptors. Accordingly, in a preferred implementation, the sympathomimetic drug is an adrenergic agonist, more preferably an α1-adrenergic agonist, and most preferably oxymetazoline. Local administration of α1 agonists is beneficial for the production of local vasoconstriction and is often used in surgery to control local hemorrhage and intranasally to promote decongestion. Exemplary α1 agonists for use with the present methods and compositions include, but are not limited to, oxymetazoline, mephentermine, metaraminol, methoxamine, naphazoline, phenylephrine, tetrahydrozoline, xylometazoline, and/or pharmaceutically acceptable salts thereof. In a preferred implementation, the α1 agonist for use with the present methods and compositions is oxymetazoline.

An "effective amount," which is also referred to herein as a "therapeutically effective amount," of a sympathomimetic drug for administration as described herein is that amount of the agonist that provides the therapeutic effect sought, such a alleviation of pain, when administered to the subject. Achieving different therapeutic effects may require different effective amounts of the drug. For example, the therapeutically effective amount of a sympathomimetic drug used for preventing a disease or condition may be different from the therapeutically effective amount used for treating, inhibiting, delaying the onset of, or causing the regression of the disease or condition. Further, the therapeutically effective amount of a sympathomimetic drug, particularly oxymetazoline, may vary dependent upon the proximity of the affected nerve to the treated skin. For example, the nerve affected by interdigital neuritis is significantly closer to the skin that the posterior tibial nerve as it passes through the tarsal tunnel. Accordingly, the therapeutically effective amount for treating interdigital neuritis may be smaller than the therapeutically effective amount to treat tarsal tunnel syndrome. In addition, the therapeutically effective amount may depend on the age and other health conditions of the subject as is well known to those versed in the disease or condition being addressed. Thus, the therapeutically effective amount may not be the same in every subject to which the sympathomimetic drug is administered.

To determine whether a level of sympathomimetic drug is a "therapeutically effective amount" to treat, prevent, inhibit, delay on set of, or cause the regression of interdigital or compression neuritis, formulations may be administered in animal models for the interdigital or compression neuritis, tarsal tunnel syndrome or carpal tunnel syndrome, and the effects may be observed. In addition, dose ranging human clinical trials may be conducted to determine the therapeutically effective amount of the sympathomimetic drug.

The term "carpal tunnel syndrome" is defined as a progressive condition causing paresthesia, pain, numbness, and other symptoms in the hand due to compression of the median nerve at the wrist in the carpal tunnel.

The term "tarsal tunnel syndrome" is defined as a compression neuropathy and painful foot condition in which the tibial nerve is compressed as it travels through the tarsal tunnel.

In a first preferred practice of the invention the composition is for topical administration. The composition comprises a sympathomimetic drug and a dermatologically acceptable vehicle. The term "dermatologically acceptable," as used herein, means that the compositions or components thereof so described are suitable for use in contact with human skin without undue toxicity, incompatibility, instability, allergic response, etc. Such a vehicle may be water, preferably sterile water, or may be organic solvent, or vegetable oil-based. Topical formulations may be formulated as a cream, ointment, lotion, poultice or gel, or they may be incorporated into a patch to be applied to the skin, the patch may have a single or multilayer construction.

The dermatologically acceptable vehicle in an ointment, cream or lotion typically will include an emulsion base. One example of a commercially available emulsion base suitable for use in the pharmaceutical compositions provided herein includes, but is not limited to, LIPODERM™ (a mixture of about 60-80% wt/wt water, with glycerin, $C_{12}$-$C_{15}$ alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, vitis vinifera (Grape) seed extract, triticum vulgare (wheat) germ oil, retinyl palmitate (vitamin A palmitate), ascorbyl palmitate (vitamin C palmitate), Pro-Lipo Multi-emulsion Liposomic System, tetrasodium EDA, phenoxyethanol, sodium hydroxymethylglycinate). PCCA, Houston, Tex. In one implementation the emulsion base is selected from the group consisting of LIPODERM; VersaBase (PCCA, Houston, Tex.); Vitamin E; Cliniderm; Dermabase (purified water, petrolatum, mineral oil, cetostearyl alcohol); Eucerin (water, petrolatum, mineral oil, ceresin, lanolin alcohol, methylchloroisothiozolinone, methylisothiazolinone); Glaxal (WellSpring Pharmaceutical Corp., Sarasota, Fla.); stearic acid cream, or any other pharmaceutical base used for topical formulations known to those skilled in the art.

The composition may further comprise at least one component selected from the group consisting of a skin penetrant, stabilizing agent, vitamin supplement, essential oil, fragrances, coloring agent, and preservative.

The composition can comprise a skin absorption enhancer to facilitate absorption of the composition through the skin of the patient. Suitable skin absorption enhancers for this purpose include pentane 1,5-diol, N-dodecyl-2-pyrrolidone and its acetate analogue, fatty acids such as oleic acid, terpenes, esters such as isopropyl myristate, khellin and khellin analogues, methyl nicotinate, MSM-decylmethylsulfoxide, diethylene glycol, citric acid, pyruvic acid, phenoxyethanol, transcutol, phosphatidyl choline, a medium chain triglyceride oil (MCT oil) and water.

The compositions can comprise stabilizing ingredients such as anti-oxidants, suitable anti-oxidants include vitamin C (ascorbic acid), or vitamin E (alpha tocopherol). The composition may also include salts to buffer the solution to physiological pH.

Suitable vitamin supplements for use in the composition include, but are not limited to, vitamin A (retinol), B group vitamins such as vitamin B1 (thiamine), vitamin B2 (riboflavin), vitamin B3 (niacin), vitamin B5 (pantothenic acid), vitamin B6 (pyridoxine pyridoxal or pyridoxamine), B7 (Biotin), B9 (folic acid) and B12 (cobalamin), vitamin C (ascorbic acid), vitamin D (calciferol), vitamin E (tocopherol) and vitamin K (phyllochinone) and combinations thereof.

Suitable essential oils for use in the composition include, but are not limited to jasmine oil, emu oil, lavender oil, tea tree oil and citrus oils.

Suitable fragrances for use in the composition include menthol, benzyl alcohol, eugenol, phenoxyethanol, isopropyl palmitate, isopropyl myristate, benzyl salicylate, phenylethyl salicylate, thymol, isoamyl salicylate, triton X-100 surfactant, benzoic acid, benzyl benzoate, methyl salicylate, phenol, oleic acid, caproic acid or carbaryl.

Conventional coloring agents suitable for use in the composition include, but are not limited to, tartrazine, quinoline yellow, sunset yellow, amaranth, ponceau 4R, erythrosine, red 2G, allura red AC, patent blue V, indigo carmine, brilliant blue FCF, fast green FCF, green S and iron oxides.

Suitable preservatives for use in the composition include, but are not limited to, parabens such as methyl and propyl paraben, sorbic acid, potassium sorbate, quaternium-15, methylchloroisothiazolinone, and Iodopropynyl butylcarbamate (IPBC) and natural preservatives such as citrus oils.

In one implementation, the present invention to provide sustained release transdermal formulations, e.g. a skin patch or a patch-needle hybrid (Microneedle). One aspect of the invention provides a transdermal device for the delivery of sympathomimetic drug, comprising an impermeable backing layer, a reservoir layer for the sympathomimetic drug or any pharmaceutically acceptable salt thereof, a pharmaceutically effective carrier, optionally a control membrane or non-controlling microporous membrane, optionally an adhesive, and optionally a protective peel strip.

Preferred topical compositions may contain a concentration of sympathomimetic drug or pharmaceutically acceptable salt thereof in an amount of from 0.1 to 5% (w/w) or from 0.2 to 1.5% (w/w) or from 0.5 to 2% (w/w) based on the total weight of the composition.

In some implementations, the formulations described herein are administered by topical administration to the foot. typically the formulations are applied to the sole of the foot, but can be applied, in addition or in the alternative, to the dorsal surface of the foot. In some implementations, the formulation is applied topically to the foot any of 1, 2, 3, 4, or 5 times per day. In some implementations, the formulation is applied topically to the foot about once or less any of about every 1, 2, 3, 4, 5, 6, or 7 day(s). In certain implementations, the frequency of application is one to four times per day for chronic, non-exercised induced. In another implementation, the formulation is applied 20 minutes before exercise in exercise induced neuritis. The expected duration of action of the formulation is about 4 hours. Therefore, additional applications may be required for sustained activity. In some implementations, the topical formulation is applied topically to the foot about once or less a day. In some implementations, the formulation is applied topically to the foot at irregular intervals, only when the subject experiences symptoms or only when the subject participates in activities that normally lead to symptoms of interdigital or compression neuritis.

In some implementations, a total amount of sympathomimetic drug, particularly oxymetazoline, less than about 200 mg is administered. In some implementations, a total amount of a sympathomimetic drug less than about 150 mg is administered. In some implementations, a total amount of sympathomimetic drug less than about 100 mg is administered. In some implementations, a total amount of sympathomimetic drug less than about 50 mg is administered. In some implementations, a total amount sympathomimetic drug less than about 25 mg is administered.

The formulations described herein may be used to deliver amounts of the sympathomimetic drug effective for treating, preventing, inhibiting, delaying on set of, or causing the regression of foot pain associated with interdigital or compression neuritis. In some implementations the formulations described herein deliver sympathomimetic drug, especially oxymetazoline, and one or more additional active agents over an extended period of time, e.g. in the form of a transdermal patch.

The topical formulations described herein may also include an additional active agent. In some implementations, the topical formulation includes one or more GABAergic agents, muscle relaxants, non-steroidal anti-inflammatories (NSAIDs), corticosteroids, analgesics, dermal anesthetics and/or tricyclic antidepressants.

GABAergic compounds include, but are not limited to, $GABA_A$ receptor ligands, including $GABA_A$ receptor agonists (e.g. bamaluzole, gaboxadol, ibotenic acid, isoguvacine, isonipecotic acid, muscimol, progabide, SL 75102, thiomuscimol, tolgabide, a benzodiazepine, chlormezanone, clomethiazole, etomidate, loreclezole, a piperidinediones, propanidid, a pyrazolopyridine, a quinazolinone, ROD-188, skullcap, stiripentol, thymol, and valerenic acid) and $GABA_A$ antagonists (e.g. bicuculline, gabazine, pitrazepin, α5IA, bilobalide, cicutoxin, cyclothiazide, DMCM, flumazenil, flurothyl, furosemide, L-655,708, oenanthotoxin, pentylenetetrazol, picrotoxin, PWZ-029, Ro15-4513, sarmazenil, suritozole, thujone, and thiocolchicoside), $GABA_B$ receptor ligands (e.g. 1,4-butanediol, baclofen, beta-phenyl-gamma-aminobutyric acid, phaclofen and saclofen), $GABA_C$ receptor ligands (e.g. progabide, tolgabide, biolbalide and TPMPA), GABA reuptake inhibitors, and GABA analogues (e.g. gapapentin, L-theanine, picamilon and pregabalin). In a preferred implementation, the topical formulation comprises one or more GABAergic agents selected from a $GABA_A$ receptor agonist, a $GABA_B$ receptor agonist (preferably baclophen) and a GABA analogue (preferably gabapentin or pregabalin).

Muscle relaxants for use in the present compositions include, but are not limited to alcuronium, atracurium, baclofen, carbolonium, carisoprodol, chlorphenesin, chlorzoxazone, cyclobenzaprine, dantrolene, decamethonium, fazadinium, gallamine, hexafluorenium, meladrazine, mephensin, metaxalone, methocarbamol, metocurine, pancuronium, pridinol, styramate, suxamethonium, suxethonium, thiocolchicoside, tizanidine, tolperisone, tubocuarine, vecuronium, or pharmaceutically acceptable salts thereof.

Tricyclic antidepressants for use in the present compositions include, but are not limited to amitriptyline, clomipramine, desapramine, imipramine, doxepine, amoxapine, maprotiline, nortriptyline, protriptyline, trimipramine and buproprion, or pharmaceutically acceptable salts thereof.

In a further aspect, provided herein are kits comprising one or more unit dose forms as described herein. In some implementations, the kit comprises one or more of packaging and instructions for use to treat one or more diseases or conditions. In some implementations, the kit comprises a diluent which is not in physical contact with the formulation or pharmaceutical formulation. In some implementations, the kit comprises any of one or more unit dose forms described herein in one or more sealed vessels. In some implementations, the kit comprises any of one or more sterile unit dose forms.

In some implementations, the kit comprises a container for the topical formulation of the present invention. Suitable containers include, for example, a bottle, a box, a blister card, a foil packet, or a combination thereof. Optionally, the kit also contains directions for properly administering the formulations. The kits can also be designed in a manner such that they are tamper resistant or designed to indicate if tampering has occurred. Optionally, the kit of the present invention can contain the topical formulation of the present invention in combination with other pharmaceutical compositions. In some implementations, the topical formulation is an individual dosage unit.

Optionally associated with the container(s) in the kits of the present invention can be a notice or printed instructions. Such printed instructions can be in a form prescribed by a governmental agency regulating the manufacture, use, or sale of pharmaceuticals or biological products, which notice reflects approval by the agency of the manufacture, use, or sale for human administration to treat a condition that could be treated by sympathomimetic drug therapy. In some implementations, the kit further comprises printed matter, which, e.g., provides information on the use of the topical formulation to treat a condition or disease or a pre-recorded media device which, e.g., provides information on the use of the topical formulation to treat a condition or disease, or a planner.

The kit can also include a container for storing other components of the kit. The container can be, for example, a bag, box, envelope or any other container that would be suitable for use in the present invention. Preferably, the container is large enough to accommodate each component and/or any administrative devices that may be accompany the topical formulations of the present invention.

VI. EXAMPLES

A. Example 1: Manufacture of Oxymetazoline Formulation

TABLE 2

| Formulation B | |
|---|---|
| 0.05% | Oxymetazoline HCl |
| 6% | Gabapentin |
| 2% | Amitriptyline HCl |
| 2% | Baclofen |
| 10% | solvent |
| 79.95% | transdermal penetrant |

Initially, the oxymetazoline and other active agents were dissolved in the solvent. The liquid, containing the active agents, was then combined with the transdermal penetrant base to form a cream for application to a patient's foot.

Eleven volunteers were provided with the formulation for application to the sole of the foot once or twice daily. Of the original eleven subjects, one was lost to follow-up and two failed to regularly apply the formulation. The remaining eight subjects, suffering from Morton's neuroma (n=6) or compression neuroma (n=2), regularly applied the formulation of Example 2 to the sole of the foot. All eight subjects reported diminished foot pain after application of the formulation. Patients reported that twice daily use provided greater pain relief than once daily or episodic use.

Three patients had follow up ultrasound during the time they were using cream and previously detectible arterial pulse was found to be undetectable on ultrasound 1 hour after cream use. These loss of detectable coincided with decrease in pain.

B. Example 2: Manufacture of Oxymetazoline Formulation

TABLE 1

| Formulation A | |
|---|---|
| 0.05% | Oxymetazoline HCl |
| 5% | solvent |
| 94.95% | transdermal penetrant |

Initially, the oxymetazoline was dissolved in the solvent. The liquid, containing the oxymetazoline, was then combined with the transdermal penetrant base to form a cream for application to a patient's foot.

A patient suffering from exercise-induced interdigital neuritis applied ointment to the sole of the foot twenty minutes prior to the neuritis producing activity. The patient reported that the foot pain diminished significantly after the first applications and continued throughout the duration of the otherwise painful activity. The patient reported that prior to beginning use of the oxymetazoline ointment, the patient could participate in no more than 30 minutes of an hour long spinning class. After use of the ointment, the patient completed the class, suffering only low grade, bearable, pain.

A different patient, suffering from tarsal tunnel syndrome, applied ointment to the inside and bottom of the heel of the affected foot once or twice daily. Prior to treatment, the patient had a sensation of "pins and needles" heel pain associated with tenderness with palpation of the posterior and plantar medial heel. The subject reported that twice daily use provided greater relief that once daily or episodic use. After 3 months of regular use, the patient stopped using the formulation as improvement in symptoms was noted. Relief of symptoms persisted for at least four months since discontinuing treatment.

A subsequent study included eleven additional patients, two of whom previously were included in the study described in Example 1 with neuroma. Of the remaining 9 study participants, five had non-exercise induced neuroma and 4 had exercise induced neuropraxia.

Of the neuroma group (n=7), two used the cream occasionally but also had cortisone injections during this time. Outcome was 100% reduction in pain and discontinuation of treatment. One patient used the oxymetazoline formulation one to three times per day for four weeks and experienced 90% reduction in painful symptoms. Two were lost to follow up. The two continuing neuroma patients used the formulation as needed for flares of pain once or twice per week. The two patients who used the formulations of both Example 1 and Example 2 stated there was no difference in the effectiveness of the preparations.

Of the neuropraxia/exercise-induced group, three experienced symptom reduction (75%-90%) during activities when using cream and one was lost to follow up.

C. Example 3: Use of Topical Oxymetazoline Formulation for Foot Pain

This example describes a study to compare the safety, tolerability and pharmacokinetics (PK) of topically applied 0.05% Oxymetazoline HCl.

The study is a double blind, vehicle-controlled, parallel-group, randomized study in patients having interdigital neuritis. Subjects receive a formulation of 0.05% Oxymetazoline or placebo. The study includes enrolling 30 subjects having non-exercise induced interdigital neuritis, commonly referred to neuroma and 30 subjects having exercise induced interdigital neuritis.

The primary outcome measure for the study is symptom reduction. The time frame for the study is 4 weeks.

Inclusion Criteria for this study include a history of interdigital neuritis. Exclusion criteria for this study include use of any skin product containing Oxymetazoline for 30 days prior to enrollment, prior surgical removal of neuroma, neuroma or interdigital neuritis symptoms without evidence of arterial pulse adjacent to neuroma. Subjects with a history of Raynaud's or other vasospastic disorders also will be excluded.

To participate in the study, subjects come to the clinic for a screening visit including ultrasound imaging of affected areas. Upon qualification, the patient returns to the clinic for 2 additional visits (3 visits total). Study medicine is self-applied 3-4 times per day to the dorsal and plantar surface of the feet and interdigital until condition improvement is achieved.

Ultrasound imaging of blood flow is monitored at each visit. Study duration is 4 weeks. Subject medication diaries are completed during the study. Study mediation is randomized to active ingredient cream or placebo cream.

Subjects complete the Visual Analogue Scale (VAS), Brief Pain Inventory (BPI), McGill Pain Questionnaire (MPQ) before receiving either control or Oxymetazoline The same questionnaires are answered again at one and four weeks later. The questionnaires provide scores for analyzing pain reduction: one VAS score, two BPI scores and five MPQ scores. Mean scores are compared to measure pain reduction.

I claim:

1. A composition for topical application to a foot or hand, said composition comprising:
   a pharmaceutically effective amount of oxymetazoline or pharmaceutically acceptable salts thereof;
   one or more muscle relaxants or pharmaceutically acceptable salts thereof selected from the group consisting of alcuronium, atracurium, baclofen, carbolonium, carisoprodol, chlorphenesin, chlorzoxazone, cyclobenzaprine, dantrolene, decamethonium, fazadinium, gallamine, hexafluorenium, meladrazine, mephensin, metaxalone, methocarbamol, metocurine, pancuronium, pridinol, styramate, suxamethonium, suxethonium, thiocolchicoside, tizanidine, tolperisone, tubocuarine and vecuronium;
   one or more antidepressants or pharmaceutically acceptable salts thereof selected from the group consisting of amitriptyline, clomipramine, desapramine, imipramine, doxepine, amoxapine, maprotiline, nortriptyline, protriptyline, trimipramine and buproprion;
   one or more GABAergic agents or pharmaceutically acceptable salts thereof selected from the group consisting of gabapentin, bamaluzole, gaboxadol, ibotenic acid, muscimol, progabide, SL 75102, thiomuscimol, tolgabide, a benzodiazepine, chlormezanone, clomethiazole, etomidate, loreclezole, a piperidinedione, propanidid, a pyrazolopyridine, a quinazolinone, ROD-188, skullcap, stiripentol, thymol, valerenic acid, bicuculline, gabazine, pitrazepin, a5IA, bilobalide, cicutoxin, cyclothiazide, DMCM, flumazenil, flurothyl, furosemide, L-655,708, oenanthotoxin, pentylene tetrazol, picrotoxin, PWZ-029, R015-4513, sarmazenil, suritozole, thujone, thiocolchicoside, 1,4-butanediol, baclofen, beta-phenyl-gamma aminobutyric acid, phaclofen, saclofen, progabide, tolgabide, biolbalide TPMPA, GABA reuptake inhibitors, gabapentin, L-theanine, picamilon or pregabalin;
   a transdermal penetrant; and
   a dermatologically acceptable vehicle;
   provided that the composition does not include a non-steroidal anti-inflammatory, an analgesic agent or a dermal anesthetic.

2. The composition of claim 1, wherein the composition comprises 0.1% (w/w) to 5% (w/w) of oxymetazoline.

3. The composition of claim 1, wherein the composition comprises 0.2 (w/w) to 1.5 (w/w) of oxymetazoline.

4. The composition of claim 1, wherein the composition comprises 0.5% (w/w) to 2% (w/w) of oxymetazoline.

5. The composition of claim 1, wherein the transdermal penetrant is pentane 1,5-diol, N-dodecyl-2-pyrrolidone and its acetate analogue, fatty acids, oleic acid, terpenes, esters, isopropyl myristate, khellin and khellin analogues, methyl nicotinate, MSM-decylmethylsulfoxide, diethylene glycol, citric acid, pyruvic acid, phenoxyethanol, transcutol, phosphatidyl choline, a medium chain triglyceride oil (MCT oil) water or combinations thereof.

6. The composition of claim 1, wherein the muscle relaxant is baclofen, the tricyclic antidepressant is amitriptyline and the GABAergic agent is gabapentin.

7. The composition of claim 6, wherein the concentration of oxymetazoline HCl is about 0.05%, the concentration of baclofen is about 2%, the concentration of amitriptyline is about 2% and the concentration of gabapentin is about 6%.

8. A composition for topical application to a foot or hand, said composition consisting essentially of:
   a pharmaceutically effective amount of oxymetazoline or pharmaceutically acceptable salts thereof;
   one or more muscle relaxants or pharmaceutically acceptable salts thereof;
   one or more antidepressants or pharmaceutically acceptable salts thereof;
   one or more GABAergic agents or pharmaceutically acceptable salts thereof; and
   a transdermal penetrant; and
   a dermatologically acceptable vehicle provided that the composition does not include a non-steroidal anti-inflammatory, an analgesic agent or a dermal anesthetic.

9. The composition of claim 8, wherein the muscle relaxant is baclofen, the tricyclic antidepressant is amitriptyline, and the GABAergic agent is gabapentin.

10. The composition of claim 9, wherein the concentration of oxymetazoline HCl is about 0.05%, the concentration of baclofen is about 2%, the concentration of amitriptyline is about 2% and the concentration of gabapentin is about 6%.

11. A composition for topical application to a foot or hand, said composition consisting of:
   a pharmaceutically effective amount of oxymetazoline or pharmaceutically acceptable salts thereof;
   one or more muscle relaxants or pharmaceutically acceptable salts thereof;
   one or more antidepressants or pharmaceutically acceptable salts thereof;
   one or more GABAergic agents or pharmaceutically acceptable salts thereof;
   a transdermal penetrant; and
   a dermatologically acceptable vehicle.

12. The composition of claim 11, wherein the sympathomimetic drug is oxymetazoline or oxymetazoline HCl, the muscle relaxant is baclofen, the tricyclic antidepressant is amitriptyline, and the GABAergic agent is gabapentin.

13. The composition of claim 12, wherein the concentration of oxymetazoline HCl is about 0.05%, the concentration of baclofen is about 2%, the concentration of amitriptyline is about 2% and the concentration of gabapentin is about 6%.

14. The composition of claim 1, wherein the concentration of oxymetazoline HCl is about 0.05%, the concentration of the muscle relaxant is about 2%, the concentration of tricyclic antidepressants is about 2% and the concentration of GABAergic agent is about 6%.

* * * * *